United States Patent [19]

Mosby

[11] Patent Number: 5,083,570
[45] Date of Patent: Jan. 28, 1992

[54] VOLUMETRIC LOCALIZATION/BIOPSY/SURGICAL DEVICE

[76] Inventor: Richard A. Mosby, P.O. Box 20554, Houston, Tex. 77225

[21] Appl. No.: 539,886

[22] Filed: Jun. 18, 1990

[51] Int. Cl.⁵ .............................................. A61B 10/00
[52] U.S. Cl. ...................................... 128/751; 604/116
[58] Field of Search ...................... 128/754, 751, 753; 604/116

[56] References Cited

U.S. PATENT DOCUMENTS

| | | | |
|---|---|---|---|
| 3,605,721 | 9/1971 | Hallac | 128/754 |
| 3,961,621 | 6/1976 | Northeved | 128/753 |
| 4,200,111 | 4/1980 | Harris | 128/751 |
| 4,230,123 | 10/1980 | Hawkins, Jr. | 128/754 |
| 4,243,048 | 1/1981 | Griffin | 128/751 |
| 4,249,539 | 2/1981 | Vilkomerson et al. | 128/754 |
| 4,461,305 | 7/1984 | Cibley | 128/751 |
| 4,742,829 | 5/1988 | Law et al. | 128/754 |
| 4,793,363 | 12/1988 | Ausherman | 128/754 |
| 4,898,178 | 2/1990 | Wedel | 128/754 |

FOREIGN PATENT DOCUMENTS 325426  1/1988  European Pat. Off. ............ 128/753

OTHER PUBLICATIONS

California Medicine, Aug. 1972, pp. 22-24.

*Primary Examiner*—Paul J. Hirsch
*Attorney, Agent, or Firm*—Neal J. Mosely

[57] ABSTRACT

A surgical device for volumetric localization, biopsy and surgical procedures consists of a tubular shaft containing an array of filaments which are preformed and preloaded as springs. The filaments when deployed by extension from the tubular shaft, after insertion through or adjacent to a tumor or other tissue mass, form a predetermined, i.e., substantially closed loop, configuration outlining, encasing and excluding a known volume of tissue, i.e., tumor or other tissue mass, from the human body for the purpose of localization, biopsy or surgical removal. The filament array configuration, when outlining, enclosing and excluding the tumor or other tissue mass, limits tissue exposure to conventional and nonconventional forms of surgery to that within the encircling filaments.

20 Claims, 2 Drawing Sheets

VOLUMETRIC LOCALIZATION/BIOPSY/SURGICAL DEVICE

BACKGROUND OF THE INVENTION

1. Field of the Invention

This invention relates to surgical devices and more particularly to a surgical device for volumetric localization, biopsy, and surgical procedures.

2. Description of the Prior Art

Presently available surgical devices for localization, biopsy, and surgical procedures use the introduction of a needle directly through the skin and are usually linear in operation. This results in haphazard localization, biopsy and surgical procedures. Tissue stabilization, tissue return and tissue amounts are not consistent. These devices offer no consideration of a third dimension in evaluation, i.e., the amount, volume or extent of a lesion, tumor or other tissue mass.

For example, in mammography, presently available localization needles are linear and placed at or near the lesion to mark the site of surgical removal. These may be stabilized with a securing barb within the breast or externally by tape or securing suture. The tip of the marking needle may move making the site incorrect for biopsy. The surgeon then follows down the path of the needle in the breast to the site of the marking tip of the localization needle. There the surgeon removes an amount of tissue based on a visual impression of the extent of the mass. This is sent to the pathologist or radiologist for evaluation as to the completeness of removal of the mass. If removal is insufficient, the surgeon has to return and remove more tissue using the same imprecise visual impression as to size and position of the tissue mass.

In biopsy procedures, presently available biopsy needles are linear and tubular and result in limited tubular biopsy material when placed into lesions, tumors and other tissue masses. This results in variable small amounts of tissue being made available for evaluation. Occasionally, no tissue is returned requiring repeat attempts causing unnecessary repeat trauma on reinsertion.

In surgery, presently available indirect surgical devices, as in suction devices, are placed into tissues and indiscriminate tissue removal takes place. Portions of organs not requiring removal are removed and/or damaged in this method. Consequently, there has been a need to provide a surgical device that allows consideration or volume, amount and/or extent of a lesion.

SUMMARY OF THE INVENTION

One of the objects of the present invention to provide a new and improved surgical device for the localization/removal of tissue in the human body for evaluation, i.e., for localization, biopsy and surgical procedures.

Another object of the invention is to provide a new and improved surgical procedure in which a tissue mass is localized through a small needle hole to totally outline the extent of such a mass, the surgeon then following the needle shaft to the mass outlined by the device and removing the device which allows controlled removal of tissue.

Another object of the invention is to provide a new and improved surgical procedure which will allow larger and more useful amounts of tissue to be removed through a small external opening and eliminate the need for repeat attempts.

Another object of the invention is to provide a new and improved surgical device for the localization/removal of tissue in the human body for evaluation, i.e., for localization, biopsy and surgical procedures, having means to outline or encase the entire volume or amount of tissue required to be removed.

Another object of the invention is to provide a new and improved surgical device for the localization/removal of tissue in the human body for evaluation, i.e., for localization, biopsy and surgical procedures, having a tubular shaft enclosing a filament array which is introduced into the body adjacent to a tumor or tissue mass and when the site of a mass is reached, the filament array is deployed into a configuration that outlines or encases the entire volume or amount of tissue required to be removed.

Still another object of the invention is to provide a new and improved surgical device for the localization/removal of tissue in the human body for evaluation, i.e., for localization, biopsy and surgical procedures, that employs a tubular shaft enclosing a preloaded filament array which is introduced into a body adjacent to a tumor or tissue mass and when the site of a mass is reached, the pre-loaded needle array is deployed into a predetermined configuration that outlines or encases the entire volume or amount of tissue required to be removed.

Still another object of the invention is to provide a new and improved surgical device for the localization/removal of tissue in the human body for evaluation, i.e., for localization, biopsy and surgical procedures, that employs a tubular shaft enclosing a preloaded filament array which is introduced into a body adjacent to a tumor or tissue mass and when the site of the mass is reached, the pre-loaded filament array is deployed into a predetermined configuration to outline, encase and limit the available tissue for removal to insure only the required volume or amount of tissue is removed.

Still another object of the invention is to provide a new and improved surgical device for the localization/removal of tissue in the human body for evaluation, i.e., for localization, biopsy and surgical procedures, that employs a tubular shaft enclosing a preloaded filament array which is introduced into the body adjacent to a tumor or tissue mass and when the site of the mass is reached, the pre-loaded filament array is deployed into predetermined configuration to outline, encase and limit and exclude tissue in the body for surgical removal by conventional means such as electrocautery or surgical excision or by newer means such as chemical, laser and sonic surgical means.

Still another object of the invention is to provide a new and improved surgical device for the localization/removal of tissue in the human body for evaluation, i.e., for localization, biopsy and surgical procedures, that employs a tubular shaft enclosing a preloaded filament array which is introduced into the body adjacent to a tumor or tissue mass and when the site of a mass is reached, the pre-loaded filament array is deployed into a predetermined configuration to outline, encase and limit and exclude tissue in the human body for surgical removal by standard direct surgical means or through a small opening.

Another object of this invention is to decrease the deformity caused by surgical intervention by decreasing the amount of tissue removed and the size of the surgical entry site.

Other objects of the invention will become apparent from time to time throughout the specification and claims as hereinafter related.

The above noted objects and other objects of the invention are accomplished by a new and improved surgical device for volumetric localization, biopsy and surgical procedures which consists of a tubular shaft containing an array of filaments which are preformed and preloaded as springs. The filaments when deployed by extension from the tubular shaft, after insertion through or adjacent to a tumor or other tissue mass, form a predetermined, i.e., substantially closed loop, configuration outlining, encasing and excluding a known volume of tissue, i.e., tumor or other tissue mass, from the human body for the purpose of localization, biopsy or surgical removal. The filament array configuration, when outlining, enclosing and excluding the tumor or other tissue mass, limits tissue exposure to conventional and nonconventional forms of surgery to that within the encircling filaments.

DESCRIPTION OF THE PREFERRED EMBODIMENT

In the various views, a surgical device is shown for localizing, biopsy or surgical excision of masses in the human body. The device is used to outline, encase and exclude tissue from the human body for the purpose of removal from the human body at the time of use or at a later time. The volumetric localization/biopsy/surgical device consists of a tubular shaft to enter the human body. Within the tubular shaft is a filament array that is pre-loaded to deploy into a pre-determined configuration to provide an area outlining, encasing or excluding human tissue. After deployment of the filament array into an excluding arrangement, conventional and non-conventional forms of surgical excision may be used to remove tissue excluded by the filament array simply by introducing the source of this form of surgical excision through the control stylet and exposing the encased tissue to the surgical source.

Figure 1:
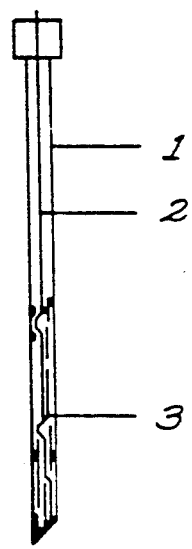
FIG. 1 is a side view of a surgical device for volumetric localization, biopsy and surgical procedures illustrating a preferred embodiment of the invention having preformed and preloaded filaments inside a tubular shaft prior to being deployed in use.

In FIG. 1 there is shown a side view of a surgical device for volumetric localization, biopsy and surgical procedures. The surgical device comprises a tubular shaft or needle A for insertion into human tissue. Tubular shaft A encloses a control stylet B which supports, manipulates and controls a filament array C which is shown in its charged or "ready" state. Filament array C comprises a plurality of individual filaments which curl into a substantially closed loop in their unstressed condition and are straightened and inserted into tubular shaft A for use in a preformed and preloaded condition.

Figure 2:
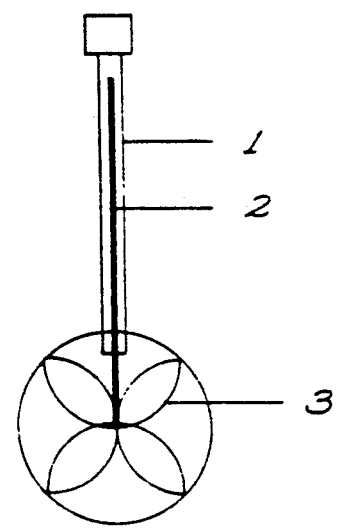
FIG. 2 is a side view of the surgical device of FIG. 1 in its deployed state with the filament array released into their functional position for encasing a tumor or other tissue mass.

In FIG. 2 the surgical device is shown in its deployed state with the tubular shaft A, the control stylet B, and the filament array C shown with the preformed and pre-loaded filaments released into their functional position. In this position, control stylet B has been moved to push the filament array C outside the end of tubular shaft A (or the shaft A has been withdrawn from stylet B) where the individual filaments curl into substantially closed loops for outlining, encasing and excluding tissue from the human body.

Figure 3:
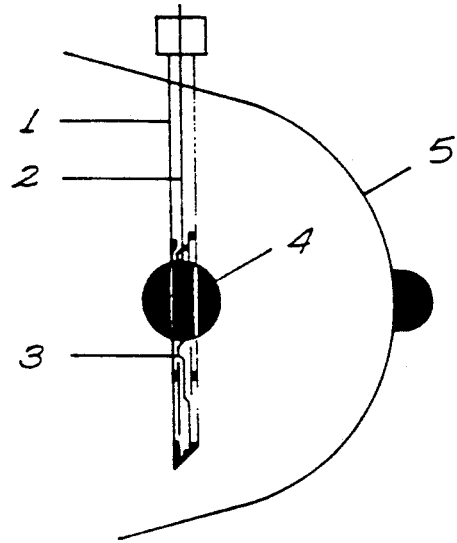
FIG. 3 is a side view of the surgical device of FIG. 1 in use with the tubular shaft entering the breast and passing through a tissue mass with the control stylet and the filament array poised prior to release.
Figure 4:
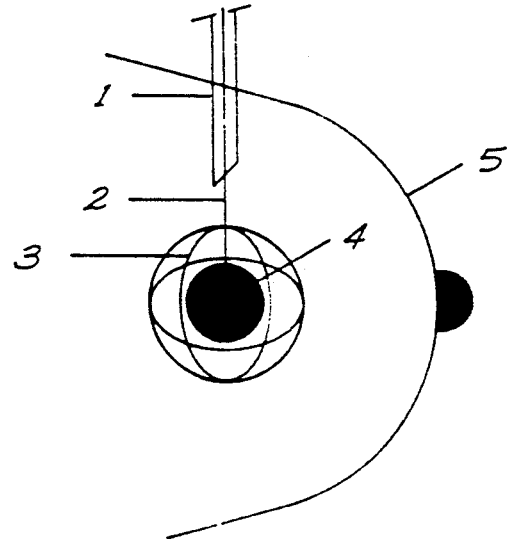
FIG. 4 is a side view of the surgical device of FIG. 1 in use with the tubular shaft withdrawn allowing release of the filament array into a functional position concentrically outlining and encasing a tissue mass in the breast.

In FIG. 3, the surgical device is shown in use with the tubular shaft A entering the breast S and passing through a tissue mass M with the control stylet B and the filament array C poised prior to release. In FIG. 4, the surgical device is shown with the tubular shaft A withdrawn allowing release of the filament array C into its functional position by advancing the control stylet B to concentrically outline and encase a mass M in the breast S.

The surgical device described above is constructed of metal, plastic and/or other durable materials having properties which permit optimum advantage to the various units of the composite. For example, tubular shaft A can be made of metal to control the spring energy of the preloaded filament array C which may be made of spring steel or spring plastic. The individual filaments may be coated with materials to enhance their limiting properties for use as with laser beam annihilation (laser surgery) as described below. The control stylet B may be made of steel or plastic, etc.

The surgical device described above, in a best use conventional surgical situation, allows a surgeon to outline the extent of a lesion, tumor or other tissue mass, prior to surgery and remove only involved tissue or tissue of concern by simply removing the deployed device, leaving uninvolved and/or adjacent tissue undisturbed. In a best use nonconventional surgical application, laser, chemical, sound, etc., may be used as agents. The localization/biopsy/surgical device limits tissue exposure to these modalities to that within the device. The device may then be removed through the tubular shaft requiring only a small external opening.

Figure 6:
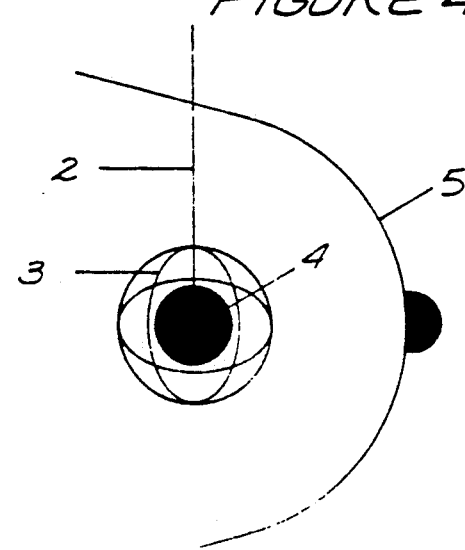
FIG. 6 is a side view of the surgical device of FIG. 1 in use with the tubular shaft totally removed and the filament array deployed to isolate the tissue mass from the breast tissue allowing a surgeon to remove the deployed filament array by following the control stylet into the area of the tissue mass.

In FIG. 3, the surgical device is shown in use with the tubular shaft A entering the breast S and passing through a tissue mass M with the control stylet B and the filament array C poised prior to release. In FIGS. 4 and 6, the surgical device is shown with the tubular shaft A withdrawn allowing release of the filament array C into its functional position by advancing the control stylet B to concentrically outline and encase a mass M in the breast S.

Figure 5:
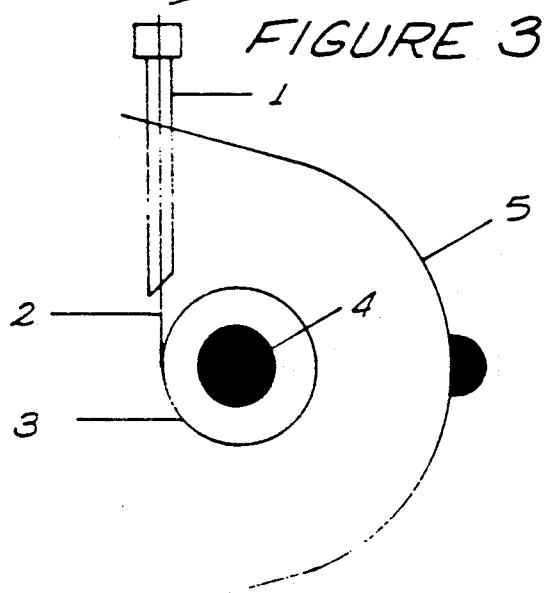
FIG. 5 is a side view of the surgical device of FIG. 1 in use with the tubular shaft withdrawn allowing release of the filament array into a functional position eccentrically outlining encasing a tissue mass in the breast.

In FIG. 5, the surgical device is placed eccentrically to the tissue mass M in the breast S. In this view, the tubular shaft A is withdrawn allowing release of the filament array C into its functional, i.e., closed loop, position by advancing control stylet B and eccentrically outlining and encasing a tissue mass M in the breast S. In FIG. 6, the surgical device is shown in use with the tubular shaft A totally removed from filament array C. This localizes a mass M in the breast S with the filament array C deployed to surround and isolate the mass M from the breast tissue S. The surgeon may then remove the deployed filament array C and encased tissue mass M by following the control stylet B into the area of the mass M.

Figure 7:
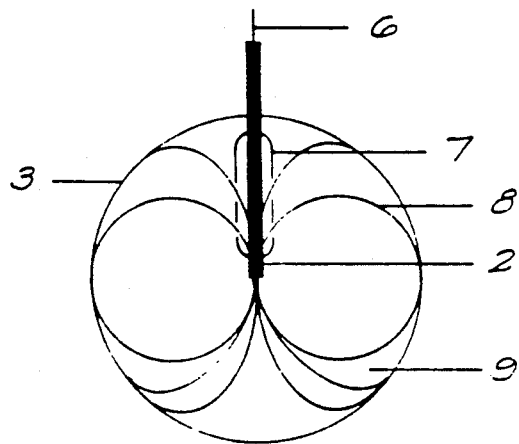
FIG. 7 is a view of an expanded use of the surgical device of FIG. 1 wherein the filament array outlines and encases a volume of tissue after being deployed and the filaments function as cutting filaments.
Figure 8:
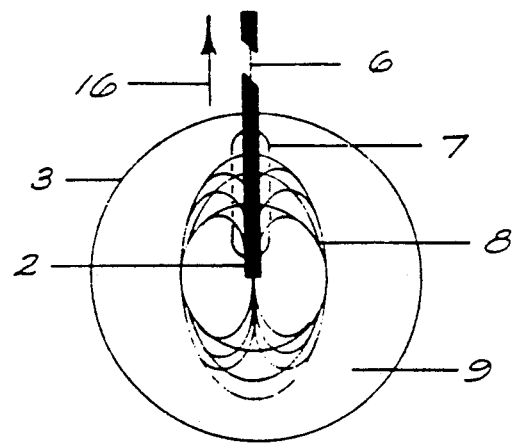
FIG. 8 shows the surgical device of FIG. 7 with a filament tip control capturing the tips of the cutting filaments and securing them so that pulling the cutting control stylet macerates the tissue mass as the arc they subtend is decreased.

In FIGS. 7 and 8, the surgical device is shown with the filaments used to perform a surgical function. In FIG. 7, the filament array C outlines and encases a volume of tissue Z after being deployed with the control stylet B as described above. The apparatus has cutting filaments F deployed by the control stylet D. In FIG. 8, the filament tip control E captures the tips of the cutting filaments F and secures them. Pulling the cutting control stylet D in the direction G macerates the human tissue Z by cutting as the arc they subtend is decreased. The tissue Z exposed to this cutting is limited by the area enclosed by the filament array C deployed by the control stylet B.

Figure 9:
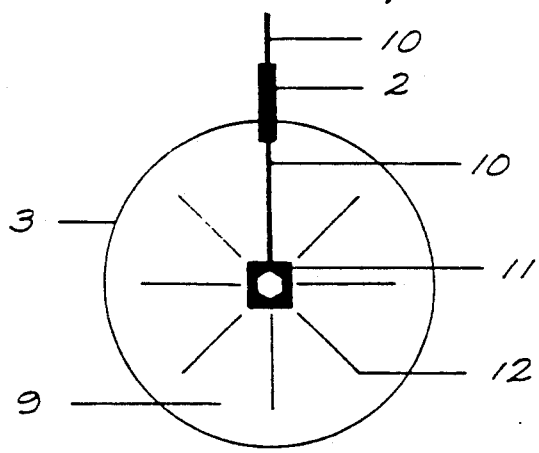
FIG. 9 shows a further expansion of the surgical device of FIG. 1 with a laser device emitting laser light introduced through the control stylet into the mass of exposed tissue and limited by the encasing filament array.

FIG. 9 shows a further expansion of the surgical device with a laser device L emitting laser light I introduced through the control stylet D by the laser control stylet H into the mass of exposed tissue Z limited by the filament array C. In the embodiment of FIG. 9, the laser beam is restricted by the pre-determined, i.e., encircling, configuration of the filament array C while allowing annihilation of the volume of tissue encased by the filament array Z.

Figure 10:
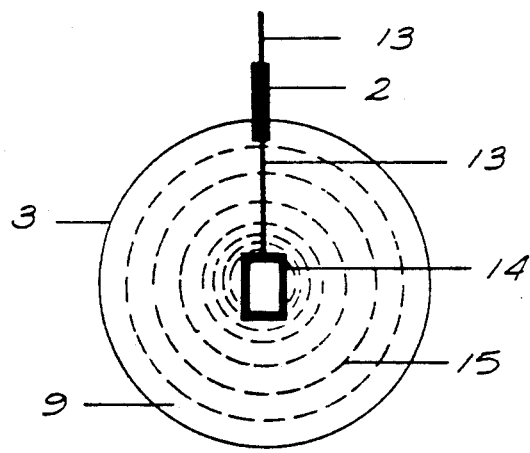
FIG. 10 shows a further expansion of the surgical device of FIG. 1 with a sound transducer emitting sound waves introduced through the control stylet into the mass of exposed tissue and limited by the encasing filament array.

FIG. 10 shows a further expansion of the surgical device with a sound transducer S1 emitting sound waves K introduced through the control stylet B by the sound control stylet J into the mass of exposed tissue Z limited by the filament array C. In the embodiment of FIG. 10, the sound waves are restricted by the predetermined, i.e., encircling, configuration of the filament array C while allowing annihilation of the volume of tissue encased by the filament array Z.

While this invention has been shown fully and completely with special emphasis on certain preferred embodiments, it should be understood that within the scope of the claims the invention may be practiced otherwise th an as specifically described herein.

I claim:

1. A surgical device for volumetric localization, biopsy and surgical procedures comprising
    a straight hollow tubular shaft of a size easily inserted into the human body through or adjacent to a tumor or tissue mass,
    a filament array positioned in said straight hollow shaft comprising a plurality of filaments of a spring deformable material having a substantially curved shape when unstressed and when straightened and positioned in said shaft being preloaded by the spring properties of the filaments, and
means supporting said array of filaments and operable to move the same relative to said hollow shaft to extend said filaments from said hollow shaft to an unstressed position where said filaments assume said substantially curved shape for outlining, encasing and excluding a known volume of tumor or other tissue mass from the human body for the purpose of localization, biopsy or surgical removal.

2. A surgical device according to claim 1 in which
said supporting means comprises a stylet movable longitudinally in said hollow shaft and supporting said filament array for movement into and out of said hollow shaft.

3. A surgical device according to claim 1 in which
said filaments have an unstressed configuration comprising a substantially closed loop.

4. A surgical device according to claim 1 in which
said supporting means comprises a stylet movable longitudinally in said hollow shaft and supporting said filament array for movement into and out of said hollow shaft, and
said filaments have an unstressed configuration comprising a substantially closed loop.

5. A surgical device according to claim 1 in which
said supporting means comprises a stylet movable longitudinally in said hollow shaft and supporting said filament array for movement into and out of said hollow shaft, and
said hollow shaft, filament array and stylet are formed of surgical steel or plastic.

6. A surgical procedure for volumetric localization, biopsy or surgical excision utilizing the surgical device of claim 1 which comprises inserting said hollow shaft into human body through or closely adjacent to a tumor or tissue mass with said filament array inside said hollow shaft,
    moving said filament array relative to said hollow shaft to extend said filaments from said hollow shaft to an unstressed position where said filaments assume said substantially curved shape outlining, encasing and excluding said tumor or tissue mass form the human body for the purpose of localization, biopsy or surgical removal, and
    subjecting the filament-encased tumor or tissue mass to removal or disintegration by a surgical or biopsy instrument.

7. A surgical procedure according to claim 6 in which
said tumor or tissue mass is removed by a conventional surgical or biopsy instrument.

8. A surgical procedure according to claim 6 in which
said tumor or tissue mass is removed by a laser surgical instrument.

9. A surgical procedure according to claim 6 in which
said tumor or tissue mass is removed by a sonic surgical instrument.

10. A surgical procedure according to claim 6 in which said tumor or tissue mass is removed by manipulation of said tumor or tissue mass encasing fibers to cause said fibers to cut or shred said encased mass for removal.

11. A surgical procedure according to claim 6 in which said encased tumor or tissue mass is removed through said hollow shaft.

12. A surgical procedure according to claim 6 in which said fibers are removed after encasing said tumor or tissue mass through said hollow shaft.

13. A surgical procedure according to claim 10 in which said hollow shaft is removed and the encased tumor or tissue mass then surgically removed.

14. A surgical procedure according to claim 6 in which said hollow shaft is inserted through said tumor or tissue mass and said filament array moved to extend said filaments from said hollow shaft to an unstressed position where said filaments assume said substantially curved shape outlining, encasing and excluding said tumor or tissue means from the human body for the purpose of localization, biopsy or surgical removal.

15. A surgical procedure according to claim 6 in which said hollow shaft is inserted closely adjacent to but outside said tumor or tissue mass and said filament array moved to extend said filaments from said hollow shaft to an unstressed position where said filaments assume said substantially curved shape outlining, encasing and excluding said tumor or tissue mass from the human body for the purpose of localization, biopsy or surgical removal.

16. A surgical procedure for volumetric localization, biopsy or surgical excision utilizing the surgical device of claim 8 which comprises inserting said hollow shaft into a human body through or closely adjacent to a tumor or tissue mass with said filament array inside said hollow shaft, moving said filament array supporting stylet longitudinally relative to said hollow shaft to extend said filaments from said hollow shaft to an unstressed position where said filaments assume said substantially curved shape outlining, encasing and excluding said tumor or tissue mess from the human body for the purpose of localization, biopsy or surgical removal, and subjecting the filament-encased tumor or tissue mass to removal or disintegration by a surgical or biopsy instrument.

17. A surgical procedure according to claim 16 in which said tumor or tissue mass is removed by a conventional surgical or biopsy instrument.

18. A surgical procedure according to claim 16 in which said tumor or tissue means is removed by manipulation of said tumor or tissue mass encasing fibers by the supporting stylet to cause said fibers to cut or shred said encased mass for removal.

19. A surgical procedure according to claim 16 in which said hollow shaft is inserted through said tumor or tissue mass and said filament array moved to extend said filaments from said hollow shaft to an unstressed position where said filaments assume said substantially curved shape outlining, encasing and excluding said tumor or tissue mass from the human body for the purpose of localization, biopsy or surgical removal.

20. A surgical procedure according to claim 16 in which said hollow shaft is inserted closely adjacent to but outside said tumor or tissue mass and said filament array moved to extend said filaments from said hollow shaft to an unstressed position where said filaments assume said substantially curved shape outlining, encasing and excluding said tumor or tissue mass from the human body for the purpose of localization, biopsy or surgical removal.

* * * * *